United States Patent [19]

Monticelli, Jr.

[11] Patent Number: 4,739,647

[45] Date of Patent: Apr. 26, 1988

[54] APPARATUS AND METHOD FOR CONTINUOUSLY MONITORING NON-CONDENSABLE GASES IN A FLOW OF MIXED GASES

[76] Inventor: F. Ronald Monticelli, Jr., 1334 Wright St., #3, Santa Rosa, Calif. 95404

[21] Appl. No.: 696,996

[22] Filed: Jan. 31, 1985

[51] Int. Cl.[4] .................. G01F 1/74; G01N 21/00
[52] U.S. Cl. ............................. 73/23; 73/29; 73/200; 73/861.04
[58] Field of Search ............ 73/23, 29, 861.04, 200

[56] References Cited

U.S. PATENT DOCUMENTS

| | | | |
|---|---|---|---|
| 3,048,035 | 8/1962 | Richards et al. | 73/200 |
| 3,234,780 | 2/1966 | Pappas | 73/29 |
| 3,566,673 | 3/1971 | Kogan | 73/23 |
| 3,881,351 | 5/1975 | Prachar | 73/861.04 |
| 3,895,915 | 7/1975 | Haldeman | 73/23 X |
| 4,178,801 | 12/1979 | Cussell et al. | 73/200 X |
| 4,312,234 | 1/1982 | Rhodes et al. | 73/861.02 |
| 4,507,875 | 4/1985 | Hirsch et al. | 73/29 X |
| 4,576,036 | 3/1986 | Huang et al. | 73/29 |

OTHER PUBLICATIONS

Michels "CO2 in Geothermal Steam" in Geothermal Resources Council Trans. vol. 2, 7/78 pp. 445-448.
McDowell "An Instrument for Measuring the Gas Concentrations in Geothermal Wells" in Geothermics vol. 3, #3 (1974), pp. 100-104.

*Primary Examiner*—Herbert Goldstein
*Attorney, Agent, or Firm*—Fliesler, Dubb, Meyer & Lovejoy

[57] ABSTRACT

An apparatus for continuous measurement of the proportion of relatively non-condensable gases in a flow of mixed gases, such as geothermal steam. The apparatus is an open system which detects the proportion of relatively non-condensable gases in a sample flow continuously. The sample flow is condensed and supplied in a tube which conditions the sample flow to consist of a series of segments of condensate and segments of uncondensed gases. The sensor senses the relative volume of the condensate and the uncondensed gases. The data processing means receives the output of the sensor and calculates the proportion of non-condensable gases in the flow of mixed gases. In the preferred embodiment, the sensor optically detects the ratio of the volume of the condensate to the volume of uncondensed gases. Also disclosed are applications of the apparatus for supplying the continuous measurement of the proportion of non-condensable gases in a flow of mixed gases for use in the monitoring of geothermal steam supplied to an end user.

26 Claims, 5 Drawing Sheets

APPARATUS AND METHOD FOR CONTINUOUSLY MONITORING NON-CONDENSABLE GASES IN A FLOW OF MIXED GASES

FIELD OF THE INVENTION

The present invention pertains to the field of measurement of the composition of a mixture of gases. Particularly, the present invention relates to the measurement of the proportion of relatively non-condensable gases in a gas mixture, such as geothermal steam.

BACKGROUND OF THE INVENTION

In some parts of the world, geothermal reservoirs are being used in the generation of energy. Typically, the geothermal reservoirs are tapped by drilling a well or several wells into the reservoir. High temperatures in the reservoir generate hot geothermal steam from naturally occurring water in the reservoir. The geothermal steam is gathered from the well or wells and transported through pipelines to a generating station, such as a steam turbine-driven electrical generator. In addition to relatively condensable water vapor, the geothermal steam typically includes relatively non-condensable gases, such as carbon dioxide, methane, nitrogen, hydrogen sulfide and hydrogen.

In the generation of power from geothermal steam using steam turbines, the proportion of non-condensable gases in the geothermal steam affects the efficiency of conversion of the energy in the geothermal steam to drive the turbine. The steam turbines operate by receiving the geothermal steam and drawing the geothermal steam through the turbine blades to cause the turbine to turn. Geothermal steam is drawn through the turbine blades typically by placing a condenser downstream from the turbine. The condenser condenses the condensable gases from the geothermal steam and creates a partial vacuum that serves to draw the geothermal steam through the turbine blades. However, the non-condensable gases in the geothermal steam tend to defeat the vacuum created by the condenser and thereby decrease the efficiency of the turbine. Therefore, it is desirable to measure the proportion of non-condensable gases in the geothermal steam so that performance criteria can be analyzed and for other reasons.

One prior art method for measuring the proportion of non-condensable gases in geothermal steam is described by Dr. Donald E. Michels ("CO2 and Geothermal Steam: A Rapid, Precise, and Accurate Field Assay Technique", *Transactions, Geothermal Resources Council*, Vol. 2, July 1978, pp. 445–448). In the Michels method, the goethermal steam line pressure drives a sample into a syringe that holds it at a known volume during equilibration. The syringe collects the non-condensable gases and equilibrates them with the condensate of the condensable gases at ice water temperature. The Michels method involves a closed system in which the geothermal steam is supplied to a known volume at a known temperature and driven by the absolute pressure of the steam line. The volume of condensate and uncondensed gases can be observed in the syringe and the proportion of non-condensable gases in the steam line can be calculated from those observed parameters.

The Michels method is only capable of supplying a maximum of six to eight determinations per hour. Thus, it is a relatively non-continuous measurement.

Another prior art closed system for measuring the proportion of non-condensable gases in a flow of geothermal steam is described by G. D. McDowell ("An Instrument for Measuring the Gas Concentrations in Geothermal Wells", GEOTHERMICS (1974) Vol. 3, No. 3, pp. 110–104). The instrument described by McDowell directly measures the partial pressure of the non-condensable gases present in a closed sample of the total mixture of geothermal steam, at a given temperature and given total pressure. This measurement is achieved by deducting the vapor pressure of distilled water at the given temperature derived from standard tables from the combined pressure of the water vapor and non-condensable gases present in the closed sample. However, this method is apparently only accurate when the non-condensable gas content of the geothermal steam is high and the steam line pressure completely stable.

SUMMARY OF THE INVENTION

The present invention provides, in one aspect, an apparatus for continuous measurements of the proportion of relatively non-condensable gases in a flow of mixed gases, such as geothermal steam. The apparatus operates as an open system and generates an essentially continuous output indicating the proportion of non-condensable gases over a wide range of gas mixtures.

The apparatus comprises a sample metering means in gas flow communication with the flow of mixed gases for supplying a sample flow of the mixed gases. The sample flow is delivered to a conditioning means for conditioning the sample flow for efficient detection of the proportion of non-condensable gases in the flow of mixed gases by a sensor means for sensing the condition of the sample flow. The sensor means generates an output continuously indicating the condition of the sample flow as it flows through the sensor means. The output of the sensor means is provided to a data processor means for processing the output to generate a measurement signal indicating the proportion of non-condensable gases in the flow of mixed gases.

In a preferred embodiment, the conditioning means includes a condensing means for condensing the relatively condensable gases in the sample flow to generate a resultant flow of a mixture of condensate and uncondensed gases. The resultant flow passes into a tube that includes an equilibration means for allowing the resultant flow to substantially equilibrate. The resultant flow flows from the equilibration means to an averaging chamber which causes the flow of condensate and uncondensed gases to accumulate into a flow of relatively large segments of condensate separated by segments of uncondensed gases flowing through a sample flow tube. The sensor means optically senses the ratio of the volume of uncondensed gases to the volume of condensate flowing through the sample flow tube and supplies an output signal to the data processing means.

In other aspects, the present invention adapts the apparatus for providing a continuous measurement of the proportion of non-condensable gases in a flow of geothermal steam for use in controlling the supply of geothermal steam to an end user, for use in measuring the quality of the geothermal steam for the production of energy, and for use in controlling the abatement of environmental pollutants among the non-condensable gases in a flow of geothermal steam.

DETAILED DESCRIPTION

With reference to the figures, a detailed description of the present invention is provided.

Figure 1:
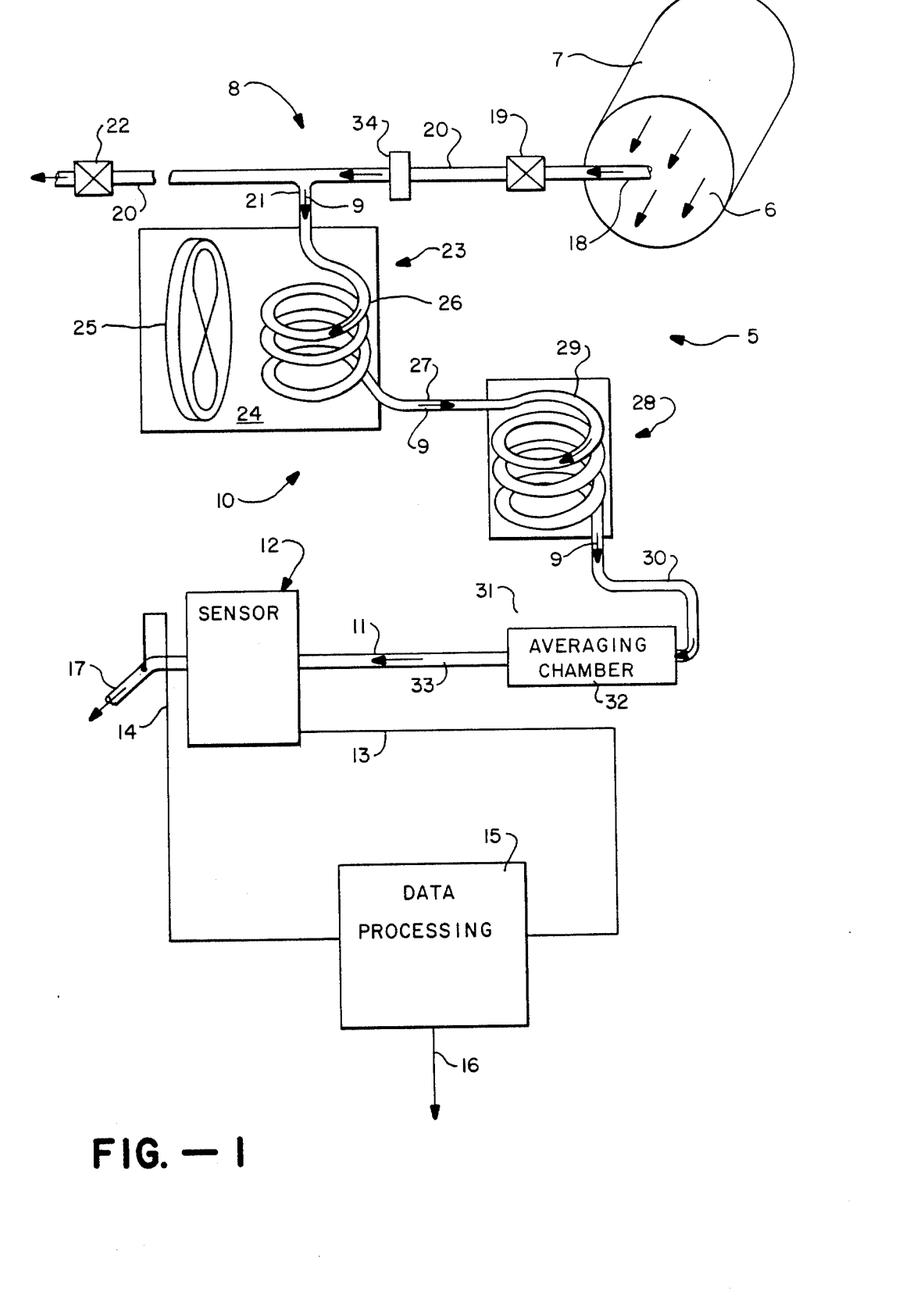
FIG. 1 is a schematic diagram of an apparatus for measuring the proportion of non-condensable gases in a flow of mixed gases according to the present invention.

FIG. 1 shows a schematic diagram of an apparatus 5 for providing a measurement of the proportion of non-condensable gases in a flow 6 of mixed gases. The flow 6 of mixed gases in the embodiments discussed in this specification is a flow of geothermal steam through a trunk 7 shown schematically in FIG. 1. The apparatus 5 is adaptable for use with other mixtures of gases as suits the needs of the user.

The apparatus 5 includes a sample metering means 8 for providing a sample flow 9 from the flow 6 of mixed gases. The sample flow 9 is supplied to a conditioning means 10 for conditioning the sample flow 9 to provide a resultant sample flow 11 that maximizes the efficiency of a sensor means 12.

The sensor means 12 detects the condition of the resultant sample flow 11 and generates a signal on line 13 which indicates the proportion of non-condensable gases in the flow 6 of mixed gases.

Also, a temperature probe 14 detects the temperature of the resultant flow 11 as it passes through the sensor means 12.

A data processing means 15 receives the signal on line 13 indicating the proportion of non-condensable gases and generates measurement signal on line 16 which provides a measurement of the proportion of non-condensable gases in the flow 6 of mixed gases.

As indicated in FIG. 1 at the drain 17, the apparatus 5 is an open system which drains the resultant sample flow 11 to the atmosphere or to a collecting means (not shown) that is open to the atmosphere for collecting and disposing of the resultant sample flow 11.

The sample metering means 8 in the embodiment shown in FIG. 1 includes a sample intake tube 18 that taps the main trunk pipeline 7 through which the flow 6 of mixed gases is passing. The sample intake tube 18 is preferably an isokinetic flow tube or other means for assuring a representative sample flow 9.

The sample intake tube 18 is connected to a first valve 19 which opens to a tube 20 having a diameter of about $\frac{1}{4}$ inch. The tube 20 includes a branch 21 consisting of a tube having a diameter of about $\frac{1}{8}$ inch. Also the tube 20 continues to a second valve 22 for controlling the amount of flow of the sample flow 9 to the branch tube 21. The second valve 22 opens to a vent to the atmosphere or to another ambient environment which can receive vented gases from the flow 6 of mixed gases. When the first valve 19 is open, the volume of flow of the sample flow 9 through the branch 21 can be controlled by varying the back pressure caused by opening or closing the second valve 22 to vary the size of the vent opening.

The branch 21 in the sample metering means 8 is placed very close to the trunk pipeline 7 in order to avoid the formation of condensate and therefore maintain the integrity of the sample flow 9.

A filter 34 is located upstream of the branch 21. The filter 34 filters particulates that may be passing through the tube 20 to prevent their contaminating the sample flow 9 and possibly damaging parts of the conditioning means 10.

The second valve 22 is located at a position remote from the conditioning means 10 as indicated by the broken lines so that the vented gases do not interfere with equipment or operators.

Thus, the sample metering means 8 supplies a sample flow 9 into a tube 21 having a diameter of about $\frac{1}{8}$ inch. The tube 21 supplies the sample flow 9 to the conditioning means 10.

The conditioning means 10 includes a condensing means 23 for condensing relatively condensable gases from the sample flow. The condensing means 23 preferably consists of a forced air-cooled condenser 24 shown schematically in the figure.

The forced air-cooled condenser 24 includes a fan 25 or other means for forcing air across a plurality of coils 26. The number of coils and the length of the tube within the forced air-cooled condenser 24 will depend on the particular condenser 24 used.

The sample flow 9 as it leaves the condenser means 23 is supplied to a tube 27 consisting of stainless steel or other suitable material and having an inner diameter of about $\frac{1}{8}$ inch. The sample flow 9 as it leaves the condenser means 23 consists of a mixture of condensate and uncondensed gases. The temperature of the sample flow 9 as it leaves the condenser means 23 preferrably falls within the range of 0° to 55° Centigrade. The pressure of the sample flow 9 drops toward atmospheric pressure as it flows through the condenser means 23.

The output of the condenser means 27 is supplied to a means 28 for allowing the sample flow 9 to substantially equilibrate. The means 28 in the preferred embodiment consists of a retention coil consisting of a tube having an inner diameter of about $\frac{1}{8}$ inch. The coil in the preferred embodiment consists of about forty to fifty feet of tubing, or a sufficient length to provide a delay time of about 20 seconds for equilibration under normal operating conditions. The loops in the retention coil 29 are maintained at a nearly horizontal angle to avoid disrupting the interspersion of the condensate and the uncondensed gases in the sample flow 9.

The sample flow 9 flowing through the retention coil 29 will tend to drop towards atmospheric pressure and stabilize. In the embodiment described, the flow of mixed gases 6 is geothermal steam, so the condensate will consist mostly of water. Thus, for a tube of about ⅛ inch inner diameter, the droplets of water will form meniscusses across the tube so that the sample flow will consist of alternating segments of condensate separated by segments of uncondensed gases. The sizes of the tubing for use with other mixtures of gases having other condensates should be varied to assure the formation of meniscusses.

The sample flow 9 as it leaves the retention coil 29 enters a tube 30 having essentially a ⅛ inch inner diameter. The tube 30 feeds a means 31 for collecting the segments of condensate and of uncondensed gases to assure a certain minimum average length of the segments of condensate. The means 31 in the preferred embodiment consists of an averaging chamber 32 which is described with reference to FIG. 2.

The averaging chamber 32 feeds a sample flow tube 33 having essentially a ⅛ inch inner diameter. The sample flow tube 33 passes through the sensor means 12. The portion of the sample flow tube 33 in the sensor means 12 is manufactured of essentially transparent tube material for facilitating optical sensors as discussed below with reference to FIGS. 3 and 4.

In sum, the conditioning means 10 consists of the condenser means 23, the means 28 for equilibrating the sample flow and the averaging chamber 26, which operate in conjunction to provide a resultant flow 11 in condition for sensing by the sensor means 12.

The conditioning means 10 and the sensor means 12 are adapted to match. Thus, for sensor means 12 other than the optical sensor of the preferred embodiment, the conditioning means 10 will have other characteristics and components. Electromagnetic or acoustic sensors may be utilized as alternatives to the optical sensor described herein.

Figure 2:
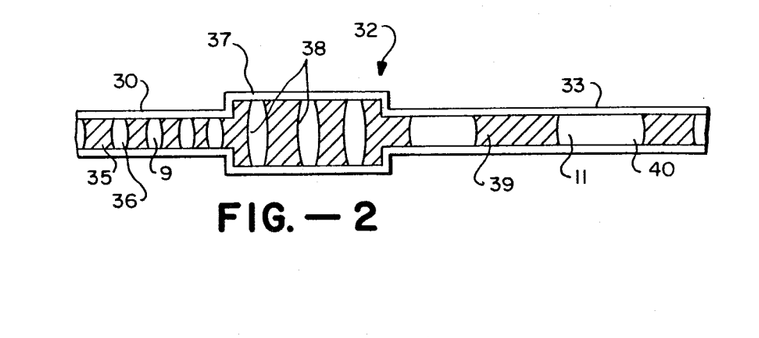
FIG. 2 is a schematic drawing of the averaging means for use in the apparatus of FIG. 1.

In FIG. 2, the averaging chamber 32 is shown. As mentioned above, a tube 30 feeds the averaging chamber 32. The tube 30 is a tube having an inner diameter of about ⅛ inch which receives the flow from the retention coil 29. The sample flow 9 in the tube 30 consists of a plurality of small segments 35 of condensate separated by segments 36 of uncondensed gases. The averaging chamber 32 consists preferrably of a tube 37 having the maximum inner diameter in which the sample flow 9 can reliably be counted on to form meniscusses 38 across tube 37. For geothermal steam, tube 37 for the averaging chamber 32 has an about ¼ inch inner diameter.

The ¼ inch tube 37 causes the sample flow 9 to form segments 39 of condensate, of a certain minimum average length, separated by segments 40 of uncondensed gases. The length of the ¼ inch tube chamber 37 should be 1 to 2 inches. The ¼ inch tube chamber 37 can be formed of stainless steel tubing or other tubing of suitable material. The ¼ inch tube chamber 37 feeds the sample flow tube 33 having an inner diameter of about ⅛ inch which supplies the resultant flow 11 to the sensor means 12. Preferably the segments of condensate 39 will be about 1 and ½ inches long under normal operating conditions when flowing through the sample flow tube 33.

Figure 3:
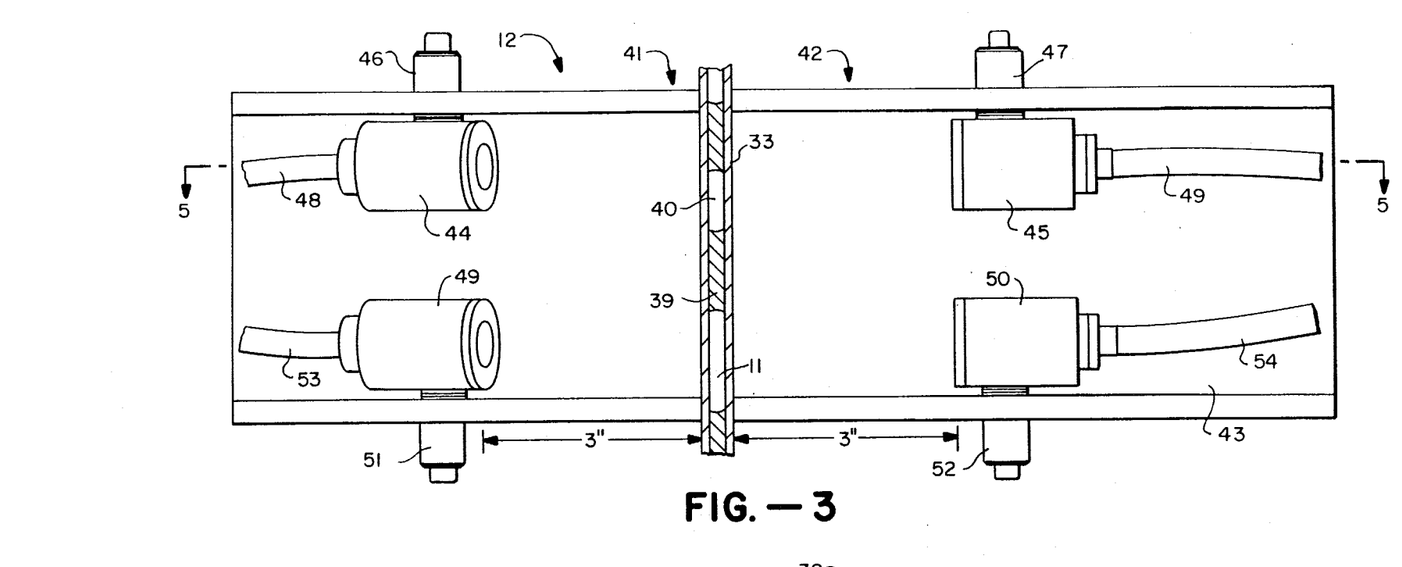
FIG. 3 is a top view of a lens subassembly for an optical sensing apparatus for use with the apparatus of FIG. 1.
Figure 4:
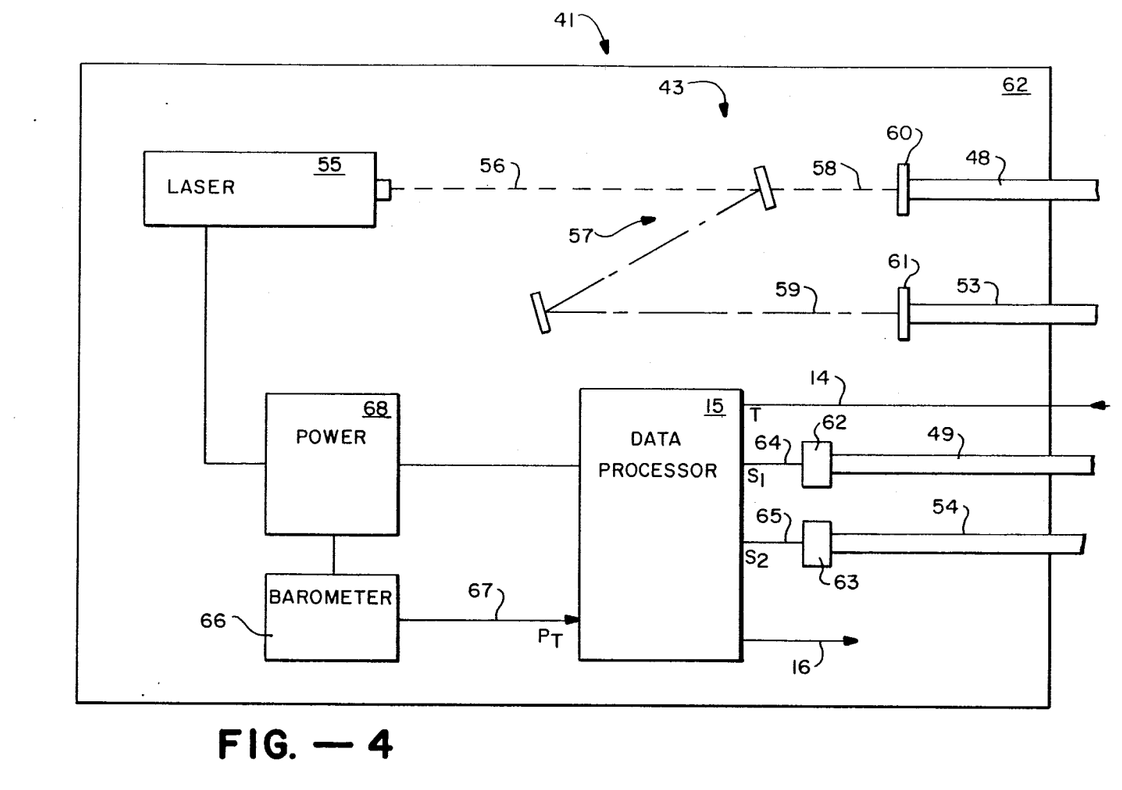
FIG. 4 is a schematic diagram of the electronic subassembly of the optical sensing apparatus for use with the lens subassembly of FIG. 3.

In the preferred embodiment, the sensor means 12 comprises an optical means 41 shown in FIGS. 3 and 4. The optical means 41 includes a lens subassembly 42 which is illustrated in FIG. 3, and an electronics subassembly 43 which is illustrated in FIG. 4.

The lens subassembly 42 includes a baseplate 43 on which a first source lens 44 and a first detector lens 45 are mounted in optical alignment. The sample flow tube 33 flows between the first source lens 44 and first detector lens 45. The first source lens 44 is mounted to the baseplate 43 by an alignment means 46 for accurately controlling the alignment of the first source lens 44. Likewise the first detector lens 45 is mounted on the baseplate 43 by an alignment means 47 for accurately aligning the first detector lens 45.

The first source lens 44 receives a beam of light through an optical cable 48. The beam of light is focused by the first source lens 44 on a point in the flow tube 33 for detecting the presence of a segment of condensate 39 or a segment of uncondensed gases 40. As explained in more detail with reference to FIGS. 5 and 6, the beam of light is focused on the first detector lens 45 when a segment of condensate passes through the beam in the flow tube 46. However, when a segment of uncondensed gases passes in front of the beam of light, the beam is deflected away from the first detector lens 45.

The first detector lens 45 focuses the beam of light when received into an optical cable 49 for delivering to the electronic subassembly 43. Thus, the optical cable 49 will deliver pulses of light to the electronic subassembly 43 having durations equal to the length of time that it takes for the segments of condensate 39 to pass in front of the beam of light supplied by the first lens means 44.

In the preferred embodiment, the lens subassembly 42 includes a second source lens 49 and a second detector lens 50 which are mounted with alignment means 51 and 52, respectively, for optically aligning the second source lens 49 with the second detector lens 50. The second source lens 49 receives a beam of light across an optical cable 53 and focuses the beam on the flow tube 33 as described with reference to FIGS. 5 and 6. The second detector lens 50 focuses the light detected into an optical cable 54 for delivering the light to the electronic subassembly 43. The second source lens 49 and second detector lens 50 are used in the calculation of the velocity of the resultant flow 11 through the flow tube 33. The data regarding the velocity of the resultant flow 11 through the flow tube 33 is useful in controlling the sample metering means 8 of the apparatus 5.

The flow tube 33 is held in optical alignment through the center of the lens subassembly 42. The lenses are spaced so that the flow tube 33 is about three inches from the first source lens 44 and second source lens 49. Also, the distance from the flow tube 33 to the first detector lens 45 and second detector lens 50 is about 3 inches. This distance may vary according to particular embodiment chosen, but it is found that satisfactory results are obtained with 3-inch spacing.

The electronic subassembly 43 of the optical sensor means 41 is shown schematically in FIG. 4.

In the preferred embodiment, the electronic subassembly 43 is mounted apart from the lens subassembly 42 in order to separate electronic components from the flow of mixed gases to prevent corrosion. In addition, if electronic components were located close to the flow of mixed gases, the danger of explosion of some combustible gases in the sample flow may be unacceptable. Other safety considerations also apply. Also, it is desirable to separate the electronic subassembly 43 so that the conditions of temperature and humidity surrounding the electronic components can be controlled with cooling or heating elements as necessary in a given environment.

The electronic subassembly 43 includes a laser 55, such as a helium-neon laser, for providing a beam of light 56. The beam of light 56 is applied to a beam splitter 57 which splits the beam into a first beam 58 for supply to the optical cable 48 which feeds the first source lens 44 in the lens subassembly 42. Also, a second beam 59 leaves the beam splitter 57 and supplies the optical cable 53 which supplies light to the second source lens 49 on the lens subassembly 42. The optical cables 48 and 53 are preferably 100 micron fiber-optic cable into which the beams of light 58 and 59 are focused. This supplies a narrow beam of light for focusing by the first source lens 44 and the second source lens 49 through the sample flow tube 46.

The laser 55, the beam splitter 57, and the means 60 for focusing the beam 58 into the optical cable 48 and the means 61 for focusing the beam 59 into the optical cable 53 are mounted on the baseplate 62 of the electronic subassembly 43 in optical alignment in order to assure reliable operation of the electronic subassembly 43.

The electronic subassembly 43 also receives the optical cable 49 from the first detector lens 45 on the lens subassembly 52 and the optical cable 54 from the second detector lens 50 in the lens subassembly 42. The optical cables 49 and 54 are made up of 600 micron fiber-optic cable 42. This facilitates the focusing of the detected light by the first and second detecting lenses 45, 50 into the fiber-optic cables 59, 54 for supplying the pulses of light to the electronic subassembly 43.

The fiber-optic cable 49 from the first detector lens 45 and the fiber-optic cable 54 from the second detector lens 50 feed an optical sensor 62 and an optical sensor 63, respectively. The optical sensors are comprised of a photovoltaic cells and amplifiers for conditioning the output of the cells for use by a data processor means 15. The optical sensors 62, 63 supply signals $S_1$, $S_2$ over lines 64, 65, respectively, to the data processor means 15. The signals $S_1$, $S_2$ on lines 64, 65 are made up of pulses having a duration equal to the amount of time that it takes a segment of condensate 39 to pass in front of the beam of light and spaced apart by the amount of time that it takes a segment of uncondensed gases 40 to pass in front of the beam of light (see FIG. 7).

The electronic subassembly 43 also receives the signal T across line 14 from the temperature probe supplying data regarding the temperature of the resultant flow 11 as it passes through the lens subassembly 42.

The electronic subassembly 43 in the preferred embodiment, includes a barometer 66 which supplies a signal $P_T$ over line 67 indicating the ambient pressure around the apparatus 5. The signal $P_T$ indicating the ambient pressure on line 67 is received by the data processing means 15. The pressure $P_T$ is needed in the generation of the measurement signal on line 16 indicating the proportion of non-condensable gases in the flow 6 of mixed gases.

A power supply 68, such as transformers connected to a standard supply line, is also located on the electronic subassembly 43 and supplies power to the laser 55, the data processor 15, and other components on the electronic subassembly 43.

Figures 5, 6, 7:
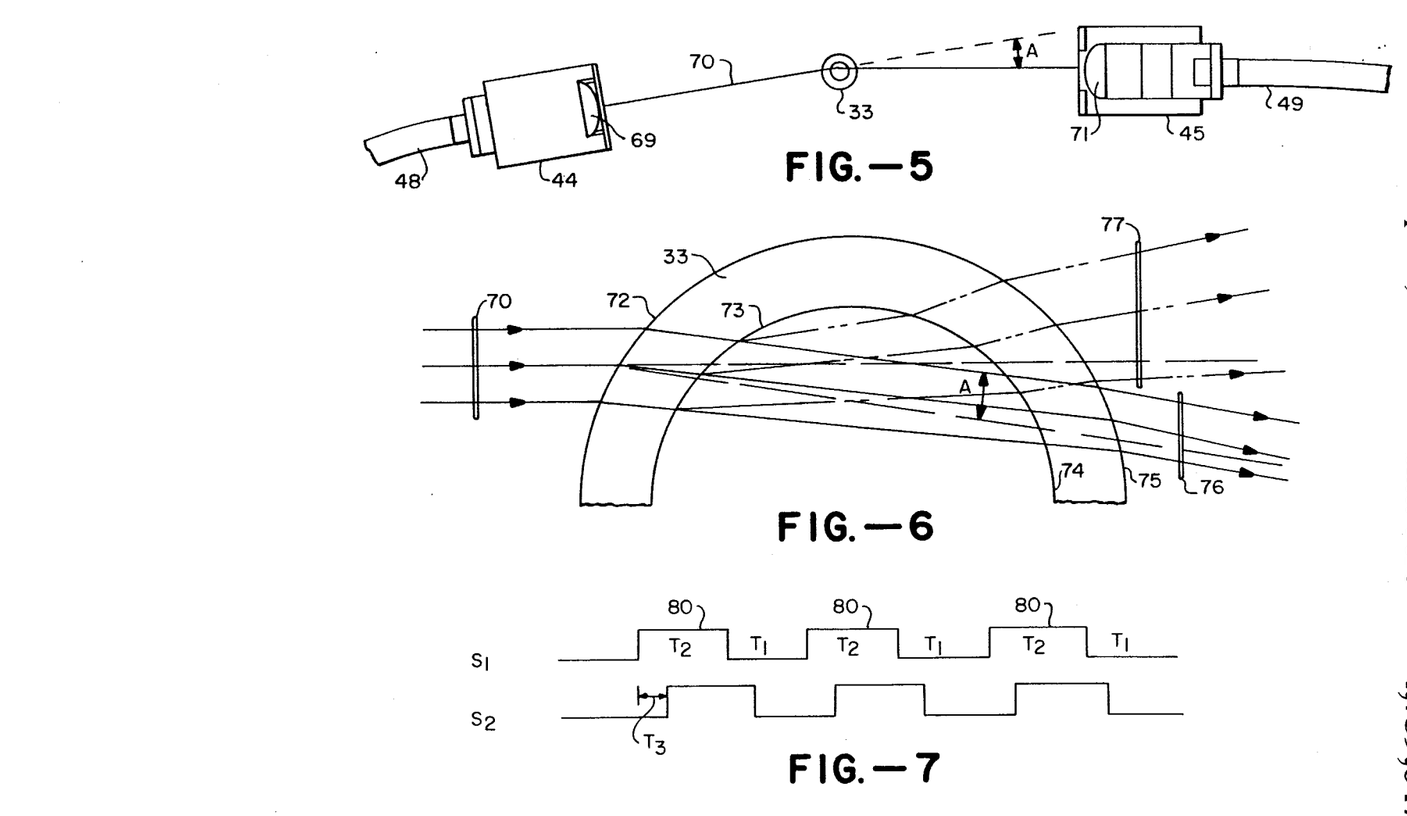
FIG. 5 is a cross-sectional view of the lens subassembly of the optical sensing apparatus taken along the line 5—5 of FIG. 2.
FIG. 6 is a schematic ray trace of the refraction of light through the sample flow tube of the optical sensing apparatus.
FIG. 7 is a graph of the output of the optical sensors in the electronic subassembly of FIG. 4.
Figure 5:
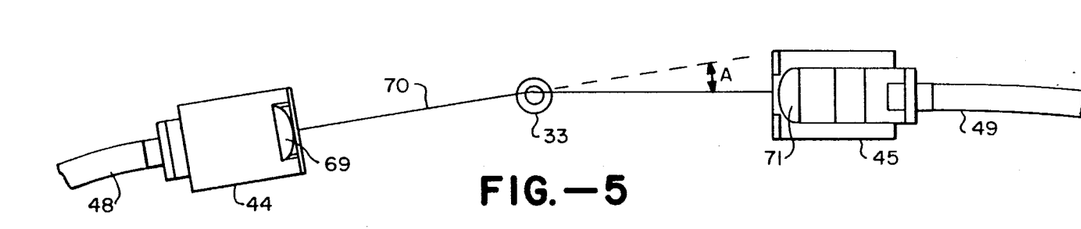
Figure 6:
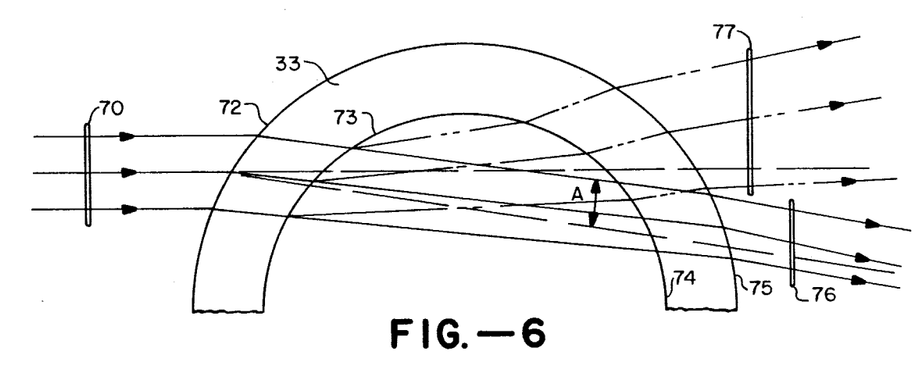
Figure 7:
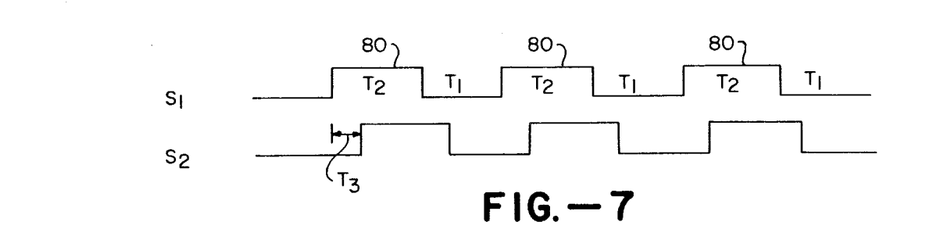

FIG. 5 shows a cross-section of the lens subassembly 42 taken along the line 5—5 in FIG. 3 for the purpose of illustrating the optical alignment of the first source lens 44, the flow tube 33, and the first detector lens 45. The first source lens 44 receives the beam of light through the optical cable 48 and focuses the beam 70 through the lens 69 on a point slightly above center in the sample flow tube 33, as explained with reference to FIG. 6. The lens 69 is preferably manufactured of a material optically transparent to helium-neon laser light in order to maximize the efficiency of the lens subassembly 42. When a segment of condensate is in the flow tube 33 at the point where the beam 70 is passing through, it is refracted at an angle A and received by the first detector lens 45 and focused into the optical cable 49. The lens 71 in the first detector lens 45 again is preferably made of a material, such as optical glass with a helium-neon anti-reflective coating, that is optically transparent to helium-neon laser light.

FIG. 6 is a schematic ray trace of the beam 70 as it passes through the flow tube 33 in the preferred embodiment. The flow tube 33 is manufactured of thin-walled Teflon tubing, or other material essentially transparent to the light of a helium-neon laser. In addition, Teflon is preferable because the index of refraction of Teflon is almost the same as the index of refraction of the condensate water passing through the flow tube 33, when the mixed flow 6 of gases is geothermal steam.

The focused beam 70 will impinge on the outer diameter 72 of the flow tube 33 and be refracted at an angle proportional to the angle of incidence on the outer diameter 72 as described by Snell's Law.

The beam 70 will pass through the wall of the flow tube 33 to the inner diameter 73 of the flow tube 33. At the inner diameter 73, if the condensate water is present, the beam will not be significantly deflected because the indexes of refraction approximately match. Thus, the beam will pass through the condensate to the inner diameter 74 on the opposite side of the flow tube 33 onto the outer diameter 75 where it will be refracted again slightly in proportion to the angle of incidence on the outer diameter 75. The resultant beam 76 will tend to converge on the angle A so that it will be received by the first detector lens 45 in the lens subassembly 42.

However, if there is not a segment of condensate in the flow tube 33 when the beam 70 impinges at the inner diameter 73, the beam will be refracted at an angle proportional to its angle of incidence on the inner diameter 73 and will pass to the inner diameter 74 on the opposite side of the flow tube 76 and be refracted once again, then through the flow tube 33 to the outer diameter 75 and refracted again. Thus, the beam 77 that will be caused if there is a segment of uncondensed gases in the flow tube 33 when the beam 70 passes through will tend to diffuse and be deflected away from the first detector lens 45.

As is illustrated in FIG. 6, the beam 70 is focused on a point in the flow tube 33 which is above the center of the flow tube 33 in order to establish angles of incidence of the beam 70 on the inner and outer diameters of the flow tube 33 to increase the difference in deflection of the beam between the conditions caused by a segment of condensate or a segment of uncondensed gases. In this manner the refraction of the light through the flow tube 33 is amplified. This amplification improves the ability to distinguish the presence of uncondensed gases from a segment of condensate in the flow tube 33. The angle A and the point of incidence of the beam 70 on the flow tube 33 are set experimentally at manufacture to optimize the apparatus 5. An angle A of about 10° has been found suitable for the embodiment described herein, so the point of incidence of the beam 70 is adjusted at manufacture to provide good results for A equal to about 10°.

The beams in FIG. 6 are represented by three lines spaced apart to illustrate the refraction of the beam. Of course the beam actually supplied should be as narrow as practical to obtain high sensitivity.

From the foregoing it can be seen that the first optical sensor 62 will generate a signal $S_1$ on line 64, such as shown in FIG. 7. Also, the second optical sensor 63 will generate a signal $S_2$ on line 65, such as shown in FIG. 7.

Signal $S_1$ on line 64 will consist of a series of pulses 80 having a duration proportional to the amount of time it takes for a segment of condensate to pass in front of the light beam 70 from the first source lens 44 and the first detector lens 45. These times are summed to equal a time $T_2$ calculated at regular intervals. The duration of time between the pulses 80 will be proportional to the amount of time it takes a segment of uncondensed gases to pass through the light beam 70. The sum of these times equals the time $T_1$ which is also calculated at regular intervals concurrent with $T_2$.

The signal $S_2$ generated by the second optical sensor 63 will a similar wave form being out of phase by a time $T_3$ from the signal $S_1$. The time $T_3$ will indicate the velocity of flow of the sample flow 11 through the flow tube 46. The time $T_3$ can be used in optimizing the flow rate of the resultant flow 11 by adjusting the sample metering means 8 described above. It is found in the preferred embodiment for geothermal steam that the flow rate should be adjusted to about between 1 and 2 feet per second. The optimum velocity of flow will depend on the average size of the segments of condensate and segments of uncondensed gases. If the flow rate is too slow, the period of time over which the times $T_1$ and $T_2$ must be measured for accurate results becomes too long. If it is too fast, a turbulent flow may be caused in the sample flow tube 33 that will disrupt the operation of the measuring apparatus 5.

The data processor means 15 receives the signal $S_1$ from which it calculates the time $T_1$ and the time $T_2$ over a set period. In the preferred embodiment the set period is one minute for normal operation. The data processor means 15 also receives the data from the temperature probe on line 14 that indicates the temperature of the condensate as it passes through the lens subassembly 42. Also, the barometric pressure $P_T$ is supplied to the data processing apparatus 15 from the barometer 66 over line 67. The data processing means 15 is made up of a microprocessor with a stored program for generating a measurement signal indicating the proportion of non-condensable gases in the flow of mixed gases.

The data processor means 15 is programmed to correct the output $S_1$ of the optical sensor for non-condensable gases remaining in the condensate and for condensable gases remaining in the uncondensed gases for the generation of a measurement signal on line 16. The approximate formula for geothermal steam is derived below for use by the data processing means 15.

The derivation of the formula for generation of the measurement signal on line 16 relies in part on the principles of gas solubility expressed in Henry's Law and in part on the standard tables for the partial pressure of water vapor at given temperatures. Values of the Henry's Law constant are approximated algebraically over the range of operating temperatures using an equation based on values for the solubility of $CO_2(g)$ in water presented in the standard tables. It is found that the solubility of other non-condensable gases in the geothermal steam may be ignored in these calculations without compromising accuracy significantly for many purposes.

Given:

Henry's Law for an ideal gas. $P_2 = X_2 P_T K_2$ (T, P, solvent)

Where:

$K_2$ = Henry's Law constant for $CO_2$ in water at one atmosphere pressure and a measured temperature
$P_2$ = Partial pressure of $CO_2$
$X_2$ = Mole fraction of the gas in the condensate
$P_T$ = Total pressure Let:

y = Total moles of $CO_2$
z = Moles of $CO_2$ in the Liquid Phase
y − z = Moles of $CO_2$ in the Gas Phase
$V_{y-z}$ = Volume of $CO_2$ in the Gas Phase (ml)
$V_{N/C}$ = Total measured volume of uncondensed gases (ml)
T = Absolute temperature of the resultant sample flow Then:

$$P_2 = \left( \frac{V_{y-z}}{V_{N/C}} \right) P_T \quad \text{(Eq. \#1)}$$

$$P_2 = \frac{(y-z)(22.4 \times 10^3 \text{ml}/M)(T/T_{STP})P_{STP}}{V_{N/C}}$$

Let:

$V_C$ = Volume of the condensate (ml)

Then:

$$X_2 = \frac{18z}{V_C} \quad \text{(Eq. \#2)}$$

According to Henry's Law:

$$\frac{P_2}{X_2} = P_T K_2$$

Substituting the values of $P_2$ and $X_2$ derived in Eq. #1 and Eq. #2 yields an equation in the form:

$$z = f(y, T, V_C, V_{N/C}, P_T, K_2) \quad \text{(Eq. \#3)}$$

$$z = \frac{(22.4 \times 10^3 \text{ml}/M) T P_{STP} V_C}{(22.4 \times 10^3 \text{ml}/M) T P_{STP} V_C + 18 K_2 V_{N/C} T_{STP} P_T} \cdot y$$

In order to correct for that proportion of non-condensable gases, principally $CO_2$, dissolved in the condensate, we generate an estimate as follows:

Let:

$V_y$ = Volume of y moles of $CO_2$ at T and $P_T$ (ml)

Then:

$V_y$ = y $(22.4 \times 10^3$ ml/M$)(T/T_{STP})(P_{STP}/P_T)$

Let:

$V_X$ = Actual volume of the non-condensable gases other than $CO_2$ in the uncondensed gases. (ml)

Then:

$V_X = V_{N/C}(P_T - P_{H2O})/P_T) - V_{(y-z)}$

Where:

$P_{H2O}$ = Partial pressure of water at T

By expansion of the above equation:

$$V_X = (V_{N/C}(P_T - P_{H_2O})/P_T) - ((y-z)(22.4 \times 10^3 \text{ml}/M)(T/T_{STP})(P_{STP}/P_T))$$

A mean value for the mole ratio of $CO_2$ in a total volume of non-condensable gases may be determined experimentally. In this example it is set to a value of 0.65. Let:

$$V_y/(V_x + V_y) = 0.65$$

From which the following equation is derived:

$$y = \frac{0.65(V_{N/C}(P_T - P_{H_2O}) + z(22.4 \times 10^3 \text{ml}/M)(T/T_{STP})P_{STP})}{(22.4 \times 10^3 \text{ml}/M)(T/T_{STP})P_{STP}}$$
(Eq. #4)

Substituting the value of y given in Eq. #4 into Eq. #3 yields Eq. #5 in the form of:

$$z = f(T, V_C, V_{N/C}, P_T, K_2)$$ (Eq. #5)

$$z = \frac{0.65(P_T - P_{H_2O})V_{N/C} T_{STP} V_C}{0.35(22.4 \times 10^3 \text{ml}/M) T P_{STP} V_C + 18 K_2 V_{N/C} T_{STP} P_T}$$

Let:
$V_z$ = Volume of z moles of $CO_2$ at T and $P_T$ (ml)
Then $V_z$, the volume by which $V_{N/C}$ should be increased to approximately account for the solubility of $CO_2$ in the condensate at T and $P_T$ is expressed by:

$$V_z = \frac{0.65 \, V_{N/C} \, V_C (22.4 \times 10^3 \text{ml}/M) \, P_{STP} \, T}{0.35(22.4 \times 10^3 \text{ml}/M) T \, P_{STP} \, V_C + 18 K_2 \, V_{N/C} \, T_{STP} \, P_T}$$

Let:
$P_{STP} = 29.92$ inches Hg
$T_{STP} = 273.15°$ K.
Then:

$$V_z = \frac{88.6 \, V_{N/C} \, V_C \, T}{47.7 \, V_C \, T + K_2 \, P_T \, V_{N/C}} \text{ (ml)}$$

The Henry's Law constant for the $CO_2$ dissolved in water, $K_2$, is found to be expressed by an equation for a hyperbola lying in the first quadrant.

$$(x-h)^2 = 4p(K_2 - m) \text{ (general form)}$$

Let:
x = temperature (°C.), $0 < x < 100$, $K_2 > 0$
Then:
$K_2 = 246 + (°C. + 40.14)^2/3.0728$
By substitution then:

$$V_z = \frac{88.6 \, V_{N/C} \, V_C (°C. + 273.2)}{(47.7 \, V_C(°C. + 273.2) + (246 + (°C. + 40.14)^2/3.0728)V_{N/C} P_T)}$$

The standard formula for determining the Gas Ratio of the volume of non-condensable gases to the volume of the mixed gases is:

$$\text{N/C Gas Ratio } (\%(V/V)) = \frac{V_{N/C}(P_T - P_{H_2O})}{1.363 \, V_C \, T + V_{N/C}(P_T - P_{H_2O})}$$

Where $V_{N/C}$ is small, e.g., less than 1%, the above equation may be simplified to:

N/C Gas Ratio
$$(V/V\%) = (V_{N/C} + V_Z)(P_T - P_{H_2O})(0.7336)/V_C T$$

A more accurate approximation of the non-condensable gas ratio is made by the inclusion of the $V_Z$ Factor:

N/C Gas Ratio
$$(V/V\%) = (V_{N/C} + V_Z)(P_T - P_{H_2O})(0.07336)/V_C T$$

The data $T_1$ and $T_2$ generated by the apparatus 5 are directly proportional to the volumes $V_{N/C}$ and $V_C$, respectively. This substitution is made in deriving the expanded form of the equation:

N/C Gas Ratio $(\%(V/V)) =$ $$(T_1 + ((88.6 \, T_1 T_2(°C. + 273.2))/(47.7 T_2(°C. + 273.2) + (246 + ((°C. + 40.14)^2/3.0728))T_1 P_T)))(P_T - P_{H_2O})(0.7336/(°C. + 273.2))/T_2$$

Assumptions made in the above derivation can be adapted to any given flow of mixed gases. Thus, for a given goethermal field, the assumed ratio of volume of $CO_2$ to the total volume of uncondensed gases may vary. So the data processing means 15 is programmed to provide the correct estimate. Likewise, other assumptions made can be adapted to a particular application.

Figure 8:
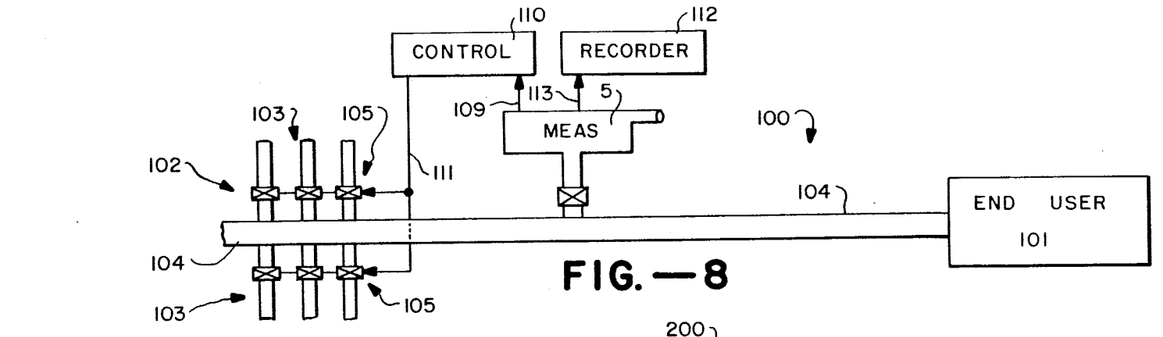
FIG. 8 is a schematic diagram of applications of the apparatus for providing a continuous measurement of the proportion of non-condensable gases in a flow of geothermal steam according to the present invention.

FIG. 8 shows a schematic diagram of an apparatus 100 for gathering geothermal steam from a plurality of wells for supply to an end user 101. The apparatus 100 includes a gathering means 102 for supplying the geothermal steam from a plurality of wells (not shown). The gathering means typically consists of a plurality of pipelines 103 which gather the geothermal steam from the remote wells and feed a trunk means 104, such as the main trunk pipeline. The trunk means 104 is preferably a large pipe for transporting large volumes of geothermal steam to the end user 101. The end user 101 typically employs the supplied steam to drive turbine generators for generating electrical energy.

The plurality of pipelines 103 is interconnected with the main pipeline 104 through a plurality of controllable valve means 105, such as motor operated valves. Preferably, the controllable valve means 105 is supplied on each of the plurality of pipelines 103, typically at the wellheads, for varying the volume of geothermal steam supplied from each of the plurality of pipelines 103. Of course, each pipeline from the plurality of pipelines 103 may gather geothermal steam from any number of geothermal wells. There may be any number of gathering stations in a given field of geothermal wells which feed any number of pipelines to the main trunk 104 through the gathering means 102 as suits the need of the particular end user or the characteristics of the geothermal reservoir.

This aspect of the present invention includes the apparatus 5 for continuously measuring the ratio of non-condensable gas to condensable gas in the geothermal steam flowing through the main trunk means 104. The apparatus 5 is mounted with the trunk means 104 through a valve 108. When the valve 108 is open, the apparatus 5 generates a measurement signal on line 109 which continuously indicates the ratio of non-condensable to condensable gas in the flow of geothermal steam.

The measurement signal generated over line 109 is communicated to a control means 110. The control means 110 communicates with the controllable valve means 105 over line 111. The control means 110 responds to the measurement signal generated by the apparatus 5 to vary the volume of geothermal steam supplied from at least one of the plurality of pipelines 103 of the gathering means 102.

Thus, the apparatus 100 for gathering geothermal steam and supplying it to an end user is able to control the ratio of non-condensable to condensable gas supplied to the end user 101 by selectively varying the volume of steam supplied by individual pipelines which feed through the gathering means 105 to the trunk 104.

Because the geothermal steam supplied from a given geothermal well may vary in the ratio of non-condensable gases to condensable gases, it is desirable to continuously measure this ratio in the trunk means 104 which supplies the gas to the end user 101. By continuously measuring this ratio, and feeding back through control means 110, the controllable valve means 105 can be manipulated to optimize the ratio of non-condensable to condensable gases supplied to the trunk means 104.

A preferred embodiment of the present invention would include a measuring apparatus 5 on each of the pipelines of the plurality of pipelines 103 of the gathering means 102. The measuring apparatus 5 on each of the pipelines would then generate data for the control means 110 for operating the controllable valve means 105.

Also illustrated in FIG. 8 is an alternative use of the apparatus 5 for providing a continuous measurement of the proportion of non-condensable gases in a flow of geothermal steam. By way of introduction, one method in which to measure the quality of geothermal steam is to measure the proportion of non-condensable gases in the steam. For instance, for persons who are selling geothermal steam to an end user 101 by volume, or by mass of steam supplied, the apparatus 5 could supply a continuous readout of the proportion of non-condensable gases which could be used in factoring the value of the steam.

In this embodiment, preferably a recorder 112 receives the output signal from the apparatus 5 on line 113 and stores the proportion of non-condensable gases per unit time which flows through the trunk 104. The recorder 112 can be a data storage device, such as a RAM, or a printout device which will provide a hardcopy output. Many other embodiments of the recorder 112 may be utilized as suits the needs of a particular user.

Figure 9:
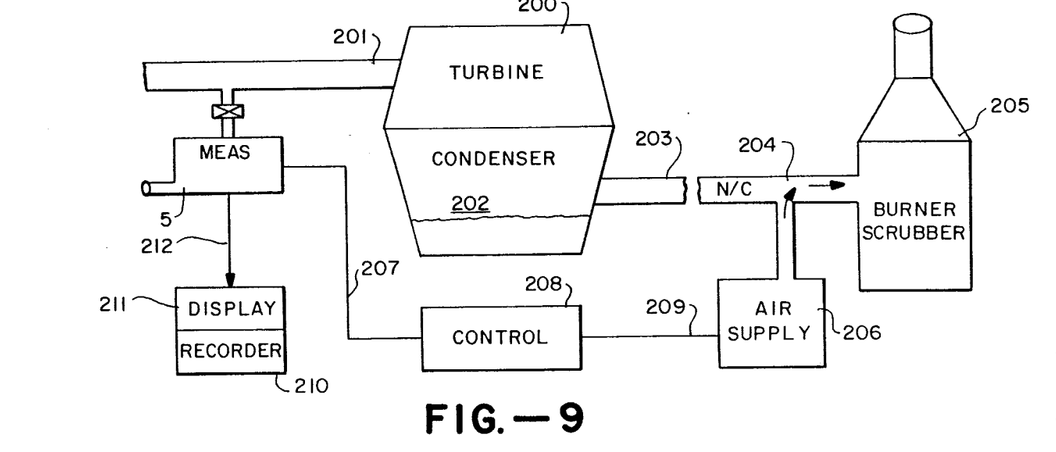
FIG. 9 is a schematic diagram of applications of the apparatus for providing a continuous measurement of the proportion of non-condensable gases in a flow of geothermal steam according to the present invention.

FIG. 9 illustrates an additional application of the apparatus 5 for providing a continuous measurement of the proportion of non-condensable gases in a flow of geothermal steam.

As mentioned in the background of the invention, a steam turbine-driven electrical generating station includes a turbine 200 which receives geothermal steam across a trunk 201. The steam is drawn through the turbine 200 by creating a partial vacuum in the condenser 202 downstream from the turbine 200. The uncondensed gases from the condenser 202 are supplied to an output pipe 203 which may pass through pumps, such as steam jet ejectors, to draw the gases out of the condenser 202. The uncondensed gases are supplied to a pipe 204. At this point in pipe 204, the flow consists largely of non-condensable gases, such as carbon dioxide, oxygen, nitrogen, hydrogen sulfide, hydrogen, and others.

Some of the non-condensable gases in pipe 204 are atmospheric pollutants, e.g., hydrogen sulfide. Therefore, the system includes an abatement system such as a burner/scrubber 204 for burning the combustible non-condensable gases to transform the majority of the pollutants to an environmentally more acceptable form.

In order to burn the non-condensable gases, a supply of oxygen, or air, 206, and fuel gases in some cases must be added to the flow of non-condensable gases. Typically the air supply 206 is generated with an air blower which is controlled to provide sufficient oxygen to burn all the fuel and combustible non-condensable gases.

However, in the event that the proportion of non-condensable gases in the geothermal steam supplied through the trunk 201 becomes large, the air supply 206 may be insufficient to keep the burner/scrubber 205 burning. Therefore, it is desirable to monitor the proportion of non-condensable gases supplied to the turbine 200 using the apparatus 5 for providing a continuous measurement of the proportion of non-condensable gases in the flow of geothermal steam. The measurement signal from the apparatus 5 is supplied across line 207 to a control means 208 for controlling the air supply 206. The control means 208 generates a control signal across line 209 to the air supply 206 for maintaining a sufficient air supply to burn the non-combustible gases in the flow of non-condensable gases in the pipe 204 that feeds the burner/scrubber 205. The control means 208 is preferably implemented with the data processing means of the measuring apparatus 5.

Alternatively, the apparatus 5 can be used as a diagnostic output for determining breakdowns in the burner/scrubber system. Thus, for instance, if the burner/scrubber 205 goes out, an operator can survey the output of a recorder 210 which has recorded the proportion of non-condensable gases supplied to the turbine 200. Also, a display 211 which receives the measurement signal of the apparatus 5 across line 212 indicating the current proportion of non-condensable gases in the flow is included in the preferred system.

In sum, the present invention provides an apparatus 5 for providing a continuous measurement of the proportion of non-condensable gases in a flow of mixed gases. The apparatus 5 has several unique applications in the field of monitoring the characteristics of geothermal steam.

The present invention is advantageous because it provides an open system measurement that requires no technician to operate once it is running, supplies an essentially continuous output, operates over a wide range of proportions of non-condensable gases in the flow of mixed gases and generates accurate results.

The foregoing description of the preferred embodiments of the invention has been presented for the purposes of illustration and description. It is not intended to be exhaustive or to limit the invention to the precise form disclosed, and obviously many modifications and variations are possible in light of the above teaching. The geothermal steam embodiment was chosen and described in order to best explain the principles of the invention and its practical application to thereby enable others skilled in the art to best utilize the invention in the various embodiments and various modifications as are suited to the particular use contemplated. It is intended that the scope of the invention be defined by the claims appended hereto.

I claim:

1. An apparatus for measuring the proportion of relatively non-condensable gases in a flow of mixed gases, comprising:
   means for condensing relatively condensable gases in the flow of mixed gases to generate a flowing combination of condensate and uncondensed gases; and
   sensing means responsive to the relative volumes of the condensate and the uncondensed gases in the flowing combination for generating an output signal the relative volume of relatively non-condensable gases in the flow of mixed gases.

2. An apparatus for measuring the proportion of relatively non-condensable gases in a flow of mixed gases, comprising:
   means for condensing relatively condensable gases in the flow of mixed gases to generate a combination flow of condensate and uncondensed gases;
   means for receiving the combination flow from the condenser means and for conditioning the combination flow to consist of a series of segments of condensate separated by segments of uncondensed gases; and
   means for sensing the condition of the conditioned flow continuously to determine the proportion of relatively non-condensable gases in the flow of mixed gases.

3. The apparatus of claim 2, wherein said sensing means includes:
   means for sensing the relative volumes of the condensate and the uncondensed gases in the combination flow.

4. The apparatus of claim 1 or 3, wherein said sensor means further includes:
   a data processing means, in communication with the means for sensing the relative volumes, for calculating the proportion of non-condensable gases in the flow of mixed gases.

5. An apparatus for measuring the proportion of relatively non-condensable gases in a flow of mixed gases, comprising:
   sample metering means for supplying a sample flow of the mixed gases;
   condenser means for condensing the relatively condensable gases in the sample flow to generate a combination flow of condensate and uncondensed gases;
   a tube for receiving the combination flow and conditioning the combination flow to consist of segments of condensate separated by segments of uncondensed gases, the segments of condensate forming meniscusses across the diameter of the tube; and
   sensor means, mounted with the tube, for sensing the relative volume of the uncondensed gases and the condensate in the resultant flow.

6. The apparatus of claim 5, wherein the tube further includes:
   averaging means for conditioning the combination flow so that an average minimum length of the segments of condensate is maintained.

7. The apparatus of claim 5, wherein the tube further includes:
   equibration means for allowing the combination flow to substantially equilibrate as it flows through the tube.

8. The apparatus of claim 7, wherein said equilibration means includes:
   a retention coil formed in the tube for delaying the combination flow prior to passing through the sensor means.

9. The apparatus of claim 5, wherein said sensor means includes:
   means for sensing the ratio of the volume of the segments of condensate to the volume of the segments of uncondensed gases in the combination flow;
   means for sensing the temperature of the combination flow; and
   means for sensing the pressure in the combination flow.

10. The apparatus of claim 5, wherein the tube opens to the atmosphere so that the pressure of the combination flow is essentially atmospheric pressure.

11. The apparatus of claim 5, further includes:
    data processing means, in communication with the sensor means, for calculating the proportion of non-condensable gases in the flow of mixed gases.

12. The apparatus of claim 11, wherein said data processing means includes:
    means for calculating the proportion of condensable gases in the segments of uncondensed gases; and
    means for calculating the proportion of non-condensable gases in the segments of condensate.

13. The apparatus of claim 12, wherein the temperature of the combination flow leaving the condenser means is in the range of 0° to 55° C.

14. The apparatus of claim 12 or 13, wherein the pressure of the combination flow near the sensor means is about atmospheric pressure.

15. The apparatus of claim 5, wherein the sensor means includes:
    optical means for detecting the relative volume of the segments of condensate and the relative volume of the segments of uncondensed gases in the combination flow.

16. The apparatus of claim 5, wherein the sensor means includes:
    acoustic means for acoustically sensing the condition of the combination flow.

17. The apparatus of claim 5, wherein the sensor means includes:
    electromagnetic means for electromagnetically sensing the condition of the combination flow.

18. The apparatus of claim 5, wherein the sensor means includes:
    first light source means for supplying a beam of light through the tube;
    first detector means in optical alignment with the light source means for detecting the beam of light when the beam passes through segment of condensate, or uncondensed gases, in the tube and not detecting the beam of light when the beam passes through a segment of uncondensed gases, or condensate, in the tube.

19. The apparatus of claim 18, further including:
    velocity detecting means for detecting the velocity of the combination flow through the tube at the sensor means.

20. The apparatus of claim 19, wherein said velocity detecting means includes:
    a second light source means for supplying a beam of light through the tube;
    a second detector means for detecting the beam of light when the beam passes through a segment of condensate, or uncondensed gases, in the tube and not detecting the beam of light when the beam passes through a segment of uncondensed gases, or condensate, in the tube;

said second light source and said second detector means mounted in combination with said first light source and said first detector means for detecting the velocity flow of the combination flow at the sensor means.

21. An apparatus for monitoring the composition of geothermal steam flowing in a pipeline, comprising:

measuring means, mounted with the pipeline, for continuously measuring the proportion of relatively non-condensable gases in the geothermal steam flowing in the pipeline and for generating a measurement signal in response to the proportion including means for condensing relatively condensable gases in the flow of mixed gases to generate a flowing combination of condensate and uncondensed gases, and means responsive to the relative volumes of the condensate and uncondensed gases in the flowing combination, for generating the measurement signal.

22. A method for measuring the proportion of relatively non-condensable gases in a flow of mixed gases, comprising the steps of:

condensing a flow of the mixed gases to generate a flowing mixture of condensate and uncondensed gases; and generating, in response to the relative volumes of the condensate and the uncondensed gases in the flowing mixture, a measurement signal indicating the proportion of relatively non-condensable gases in the flow of mixed gases.

23. A method for measuring the proportion of relatively non-condensable gases in a flow of mixed gases, comprising:

condensing a flow of the mixed gases to generate a flowing mixture of condensate and uncondensed gases;

detecting the relative volumes of the condensate and uncondensed gases in the flowing mixture;

detecting the temperature and pressure of the mixture of condensate and uncondensed gases;

calculating the proportion of condensate remaining in the uncondensed gases at the detected temperature and pressure;

calculating the proportion of said relatively non-condensable gases in the condensate based on Henry's Law; and generating a measurement signal indicating the proportion of non-condensable gases in the flow of mixed gases.

24. The method of claim 23, where Henry's Law Constant $K_2$ is approximated algebraically for a range of temperatures greater than the freezing point of the condensate.

25. The method of claim 23, wherein said flow of mixed gases is geothermal steam, and further comprising the step of:

equilibrating the mixture of condensate and uncondensed gases toward ambient pressure and temperature; and Henry's Law Constant $K_2$ is approximated by a hyperbola in the first quandrant over the range of temperatures from 0° to 55° Celcius.

26. The method of claim 25, wherein said flow of mixed gases is geothermal steam, and Henry's Law Constant $K_2$ at one atmosphere is approximated substantially by the following equation:

$$K_2 = 246 + \frac{(T + 40.14)^2}{3.073}$$

for T equal to the temperature of the mixture of condensate and uncondensed gases detected over the range of T=0° to 55° Celcius.

* * * * *